United States Patent [19]
Watanabe

[11] Patent Number: 5,665,308
[45] Date of Patent: Sep. 9, 1997

[54] URINE OCCULT BLOOD TEST APPARATUS

[76] Inventor: Hiroki Watanabe, 30-20, Hieidaira 3-chome, Ootsu-shi, Shiga-ken, Japan

[21] Appl. No.: 541,272

[22] Filed: Oct. 12, 1995

[30]  Foreign Application Priority Data

Jan. 27, 1995 [JP] Japan .................................. 7-012019
[51] Int. Cl.⁶ .......................... A61M 25/09; G01N 33/49
[52] U.S. Cl. ............................ 422/58; 128/771; 128/768
[58] Field of Search .............................. 128/760, 771, 128/768; 422/58, 61

[56]    References Cited

U.S. PATENT DOCUMENTS 4,344,439   8/1982   Jacobellis ............................... 128/771
4,756,708   7/1988   Martin ..................................... 128/760

*Primary Examiner*—Lyle A. Alexander
*Attorney, Agent, or Firm*—Koda and Androlia

[57]            ABSTRACT

A urine occult blood test apparatus includes an insert member insertable in a working channel of a cystoscope and a urine occult blood test member provided at a tip portion of the insert member. The urine occult blood test member is covered during insertion of the insert member and exposed after the insertion. The urine occult blood test apparatus is inserted and advanced to just before the ureteral opening by using the cystoscope. It is directly observed that urine coming out from the ureteral opening is received by the tip portion of the insert member having the urine occult blood test member. Therefore, such a urine occult blood test enables to confirm which is bleeding, the right or left kidney or the right or left ureter.

7 Claims, 10 Drawing Sheets

URINE OCCULT BLOOD TEST APPARATUS

BACKGROUND OF THE INVENTION

The present invention relates to a urine occult blood test apparatus for detecting bleeding from a urinary tract, especially bleeding from an upper urinary tract.

Reaction paper for inspecting presence or absence of urine occult blood has been available on the market. This reaction paper is directly immersed in a urine sample to ascertain presence or absence of urine occult blood in the sample.

In the conventional method of dipping the known reaction paper directly in the sampled urine, it is detectable whether or not occult blood exists in the urine discharged from a bladder. However, it is impossible to ascertain which is responsible for bleeding, the right kidney, the left kidney, the right ureter or the left ureter which supply urine into the bladder.

It is hence a primary object of the present invention to provide a urine occult blood test apparatus capable of ascertaining which is bleeding, the right or left kidney or the right or left ureter.

In order to achieve the object, a urine occult blood test apparatus of the present invention includes an insert member and a urine occult blood test member. The insert member is designed to be insertable in a working channel of a cystoscope and has the urine occult blood test member at its tip portion. The urine occult blood test member is covered during the insertion of the insert member and exposed after the insertion.

A urine occult blood test apparatus of the present invention may include a catheter and a urine occult blood test member. The catheter is designed to be insertable in a working channel of a cystoscope and has the urine occult blood test member at its tip portion. The urine occult blood test member is covered with a soluble substance which is dissolvable in several minutes and harmless to a human body.

Furthermore a urine occult blood test apparatus of the present invention may include a catheter insertable in a working channel of a cystoscope, a wire slidably inserted in the catheter, and a urine occult blood test member at the tip portion of the wire. The tip portion of the wire is designed to be retractable in or projectable out from the tip portion of the catheter.

Being constituted as stated above, the urine occult blood test apparatus of the present invention is inserted to just before a ureteral opening by using a cystoscope, so that urine coming out of the ureteral opening can be received by the tip portion of the insert member with the urine occult blood test member and observed directly.

The above and other objects, features and advantages of the present invention will become apparent from the following description in conjunction with the accompanying drawings.

DETAILED DESCRIPTION OF THE PREFERRED EMBODIMENTS

Figure 1:
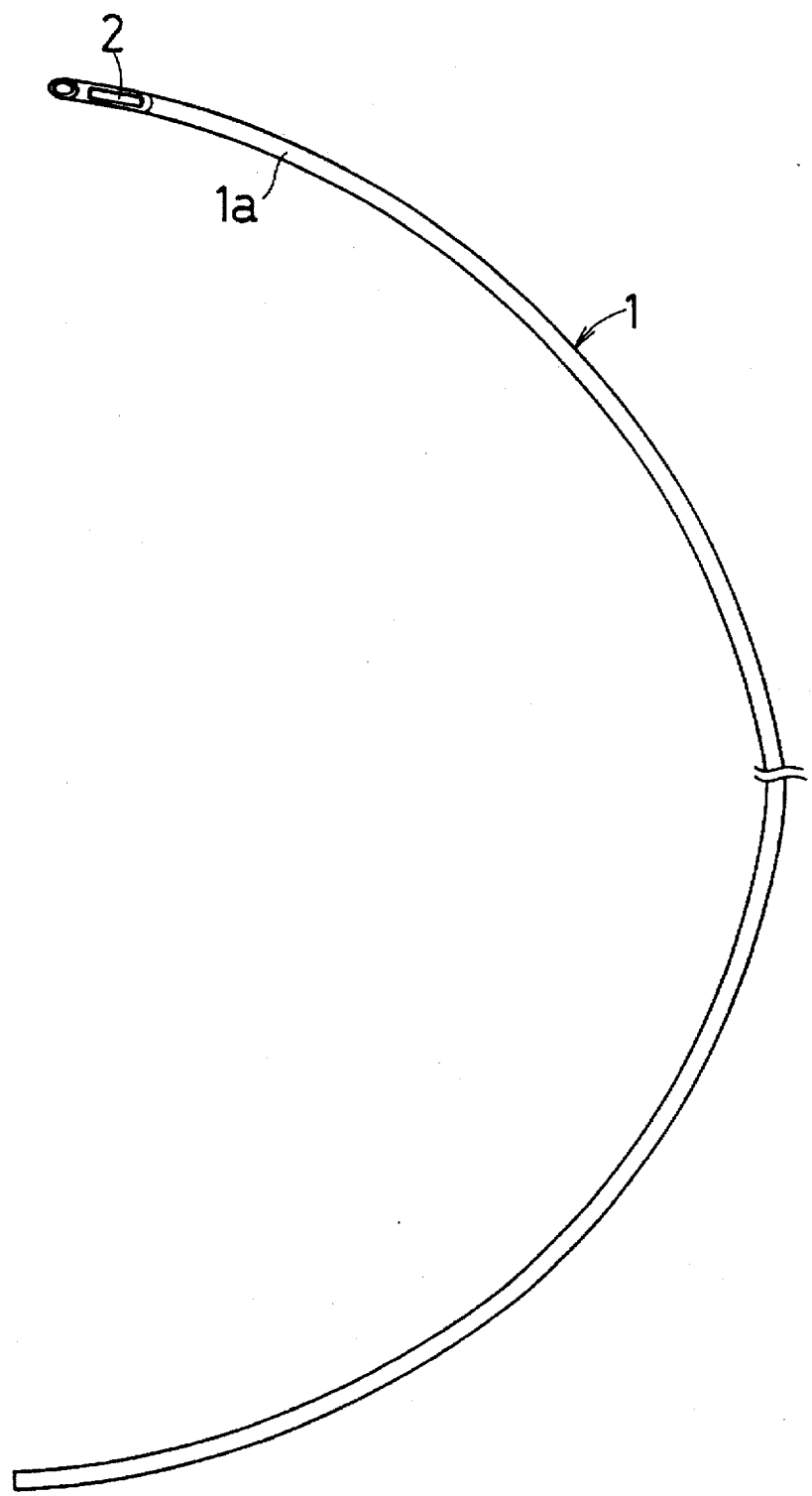
FIG. 1 is a plan view, partially omitted, showing a first embodiment of a urine occult blood test apparatus of the present invention.
Figure 2:
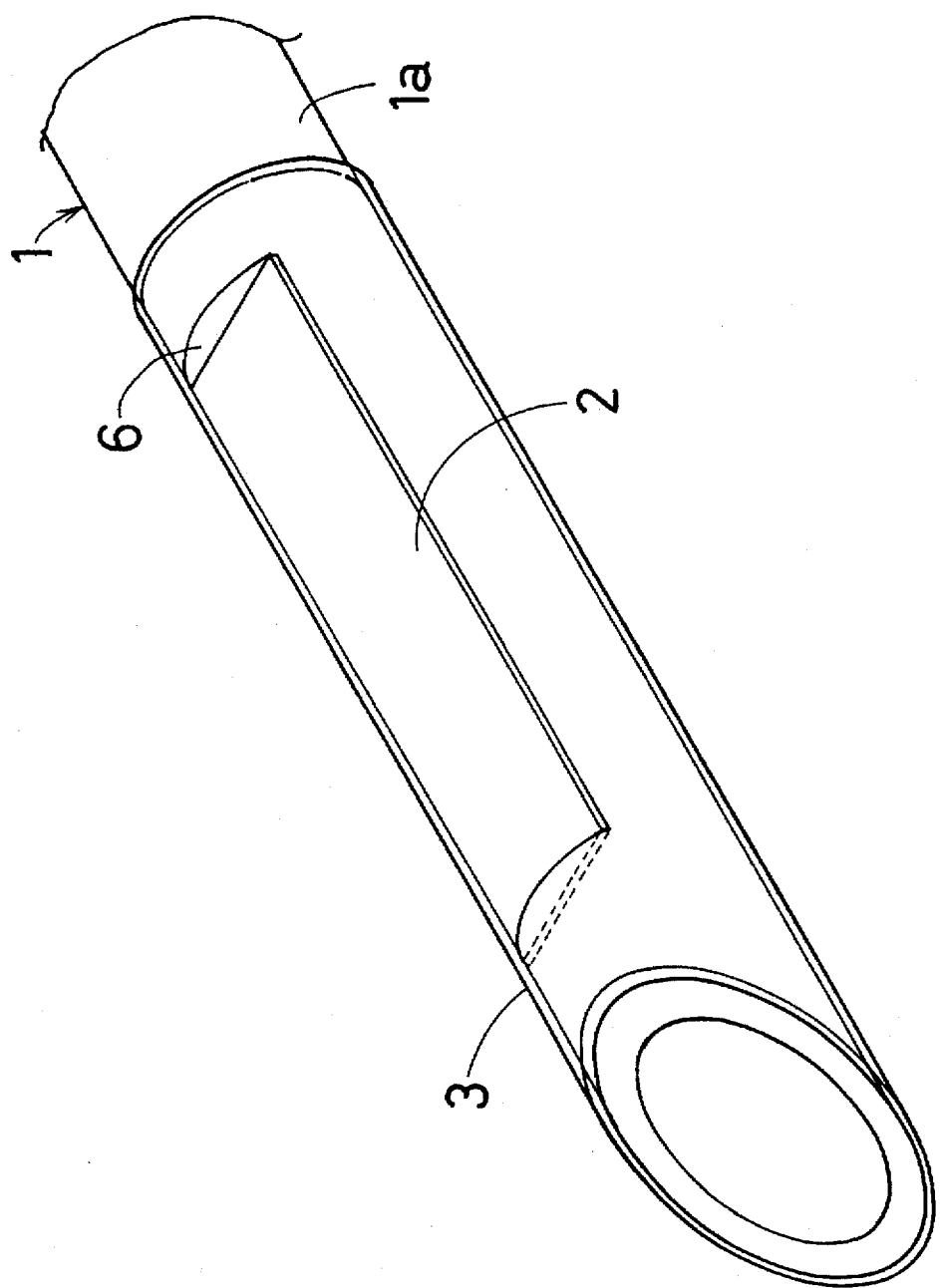
FIG. 2 is an explanatory view showing a state in which the urine occult blood test member is held at a tip portion of a catheter in the first embodiment of the urine occult blood test apparatus.

A first embodiment of a urine occult blood test apparatus of the present invention is illustrated in FIGS. 1 and 2. The urine occult blood test apparatus includes a insert member 1 and a urine occult blood test member 2. The insert member 1 is insertable in a working channel of a cystoscope. The urine occult blood test member 2 is held at a tip portion of the insert member 1. The surface of the test member 2 is covered while the insert member 1 is being inserted. After the insertion is completed, the surface is exposed.

More particularly, the insert member 1 is a catheter 1a which is flexible enough to be inserted into a working channel of a cystoscope. At a tip of the catheter 1a, there is a urine occult blood test member 2 covered with soluble substance 3 which is harmless to a human body.

Figure 3:
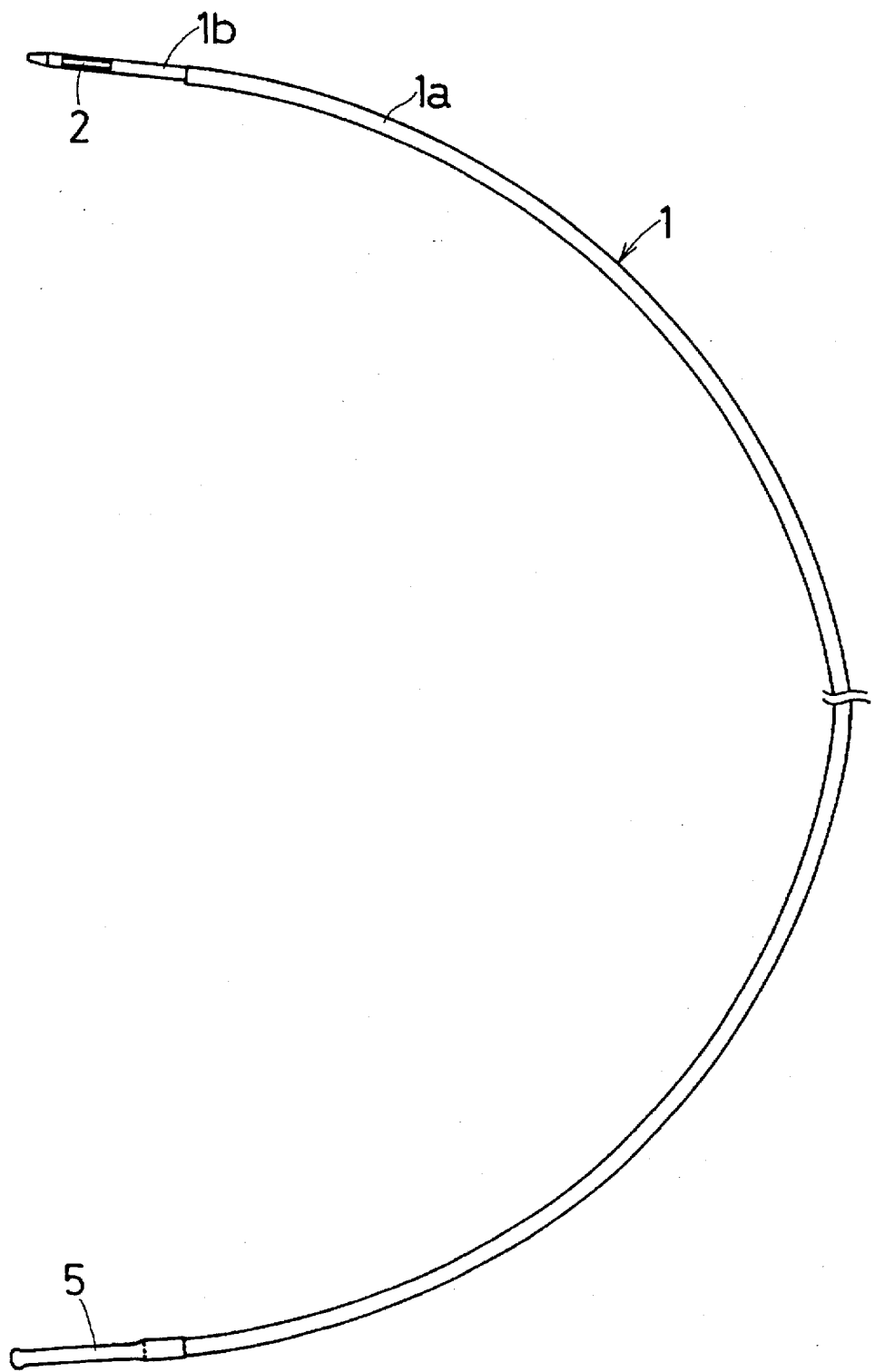
FIG. 3 is a plan view, partially omitted, of a second embodiment of a urine occult blood test apparatus of the present invention, which shows a state in which a tip portion of a wire is exposed from the tip portion of a catheter.
Figure 4:
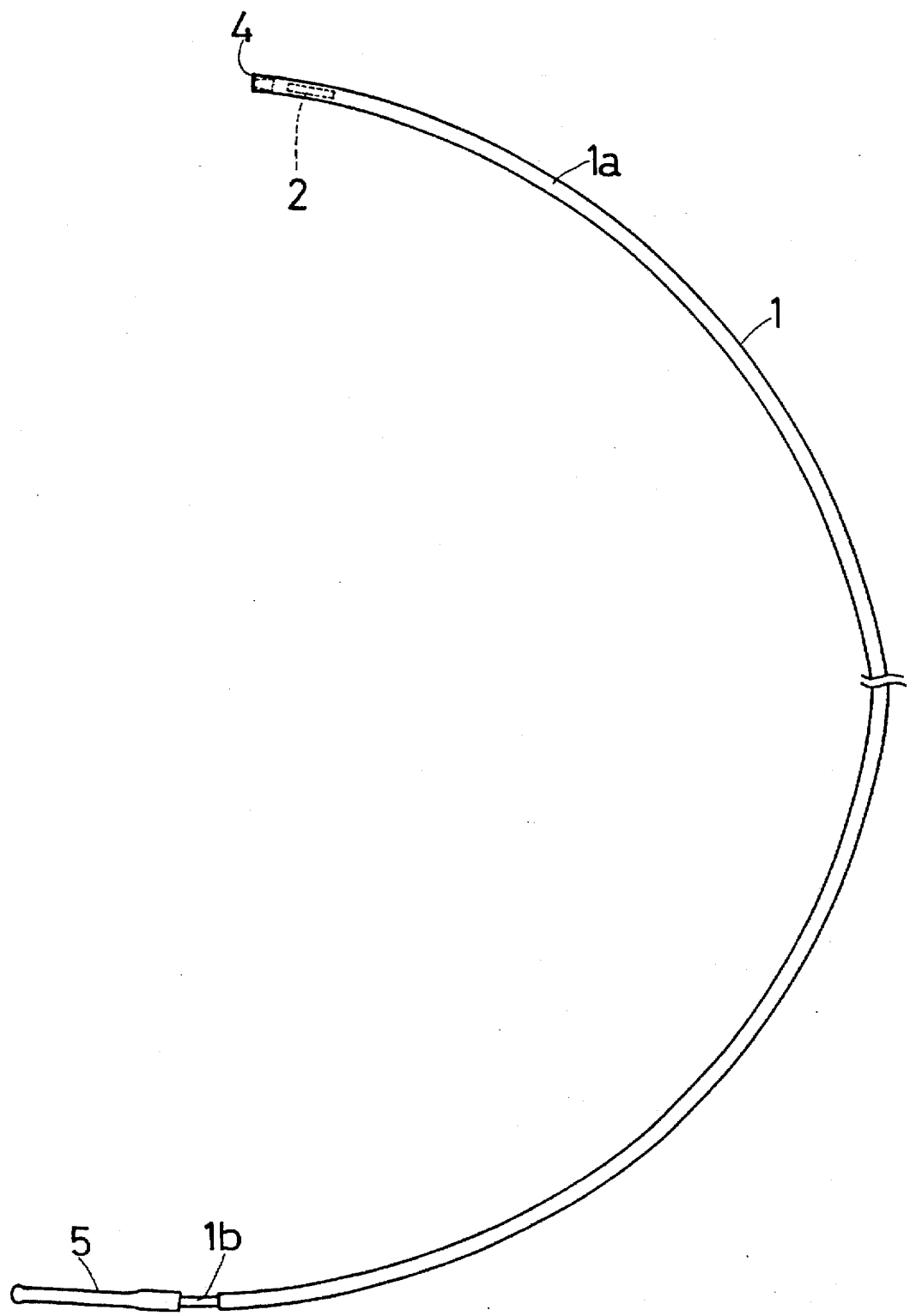
FIG. 4 is a partially omitted plan view of the second embodiment of the urine occult blood test apparatus of the present invention, which shows a state in which the tip portion of the wire is retracted in the tip portion of the catheter.
Figure 5:
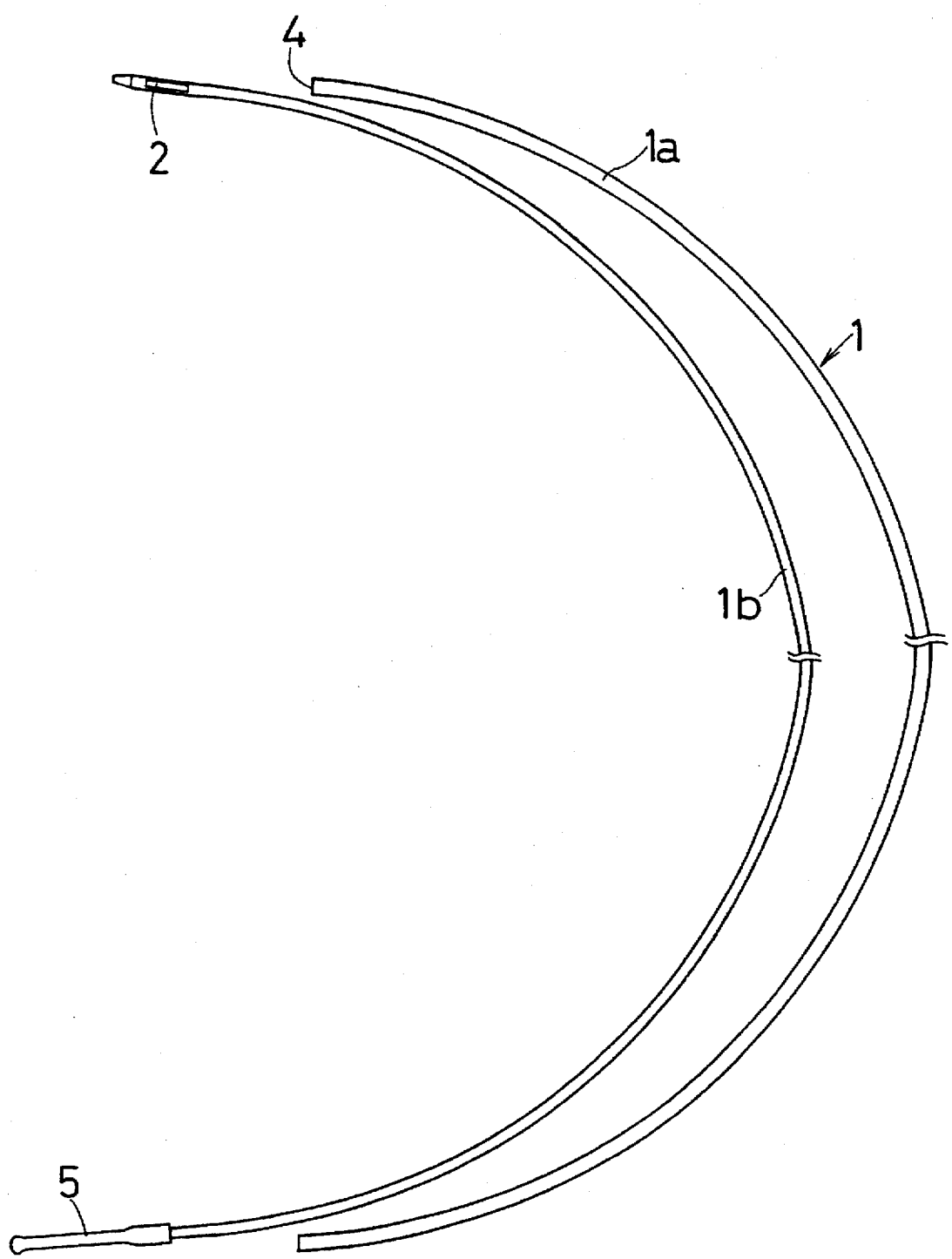
FIG. 5 is a partially omitted plan view of the second embodiment of the urine occult blood test apparatus of the present invention, wherein the wire is completely drawn out of the catheter.

FIGS. 3 to 5 illustrate a second embodiment of a urine occult blood test apparatus of the present invention. In this embodiment, an insert member 1 is composed of a catheter 1a and a wire 1b. The catheter 1a has an openable valve 4 at its tip portion. The wire 1b is inserted slidably in the catheter 1a and possesses an operation member 5 at its rear end portion (opposite to its tip portion). Thus formed insert member is insertable in a working channel of a cystoscope. A urine occult blood test member 2 is provided at the tip portion of the wire 1b. The tip portion of the wire 1b is projectable from and retractable in the tip portion of the catheter 1a. It is designed that, while the insert member 1 is being inserted, the surface of the urine occult blood test member 2 is covered, and after the insertion, it is exposed.

As far as the catheter 1a is flexible enough to be inserted in a working channel of a cystoscope, material of the catheter 1a is not particularly limited. The catheter 1a measures about 2 to 3 mm in diameter and about 35 to 45 cm in length.

Also, as far as the wire 1b is flexible enough to be inserted into the catheter 1a, material of the wire 1b is not particularly limited. The wire 1b has diameter of about 1 to 2 mm and length of about 40 to 50 cm.

Figure 6:
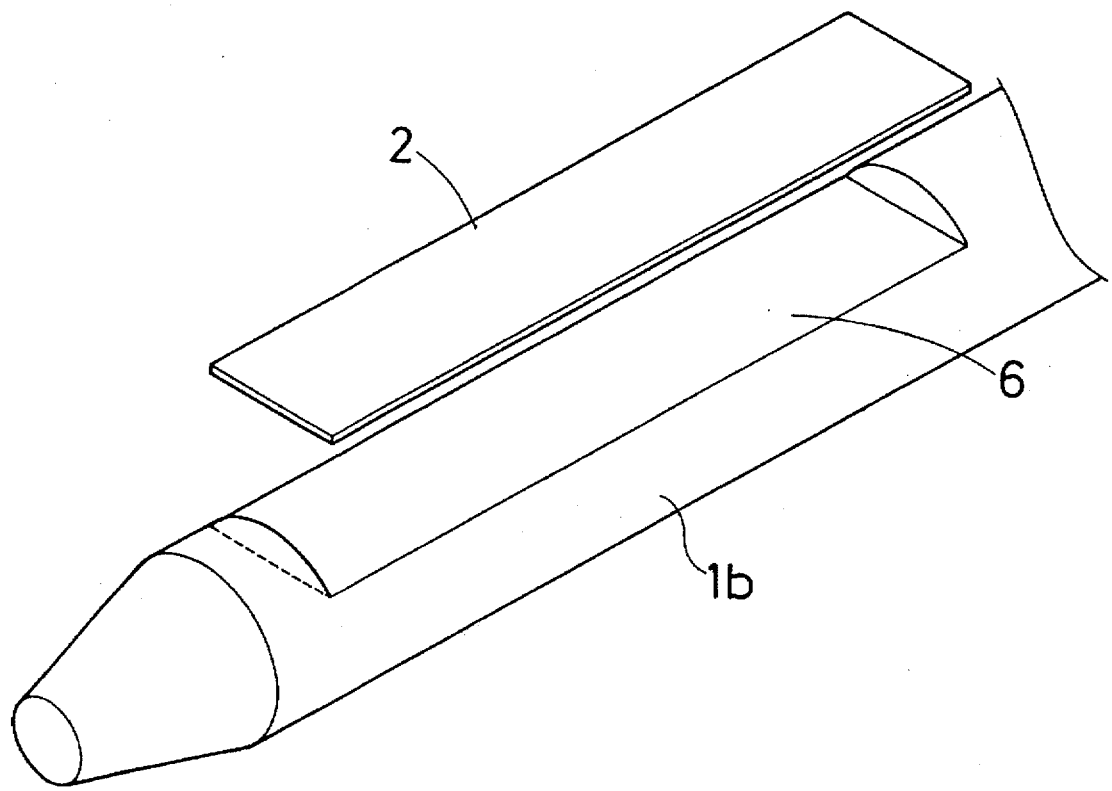
FIG. 6 is an explanatory view showing a state in which the urine occult blood test member is held at the tip portion of the wire in the second embodiment of the urine occult blood test apparatus.

Referring to FIGS. 2 and 6, the urine occult blood test member 2 is held at the tip portion of the insert member 1 in a manner that it is adhered or applied to settle in a groove 6 formed on a side surface of the tip portion of the catheter 1a or the wire 1b. The urine occult blood test member 2 is favorably to be fabricated in a size of about 1 mm in width and about 5 mm in length. The groove 6 is formed in a size in which the urine occult blood test member 2 settles precisely. In the embodiments, as the urine occult blood test member 2, urine occult blood test material on the market was cut and used. Such material includes Rubstics (urine test paper of Miles Sankyo Kabushiki Kaisha). However, it is, of course, not limitative.

The soluble substance 3 is required to be dissolved in several minutes. A starch film is used in the embodiment. However, as far as it is harmless to a human body, it is not limited to it. The reason for several minutes as the dissolving time of soluble substance 3 is because it takes time to insert the insert member 1 into a working channel of a cystoscope and advance it to just before a ureteral opening.

Figure 7:
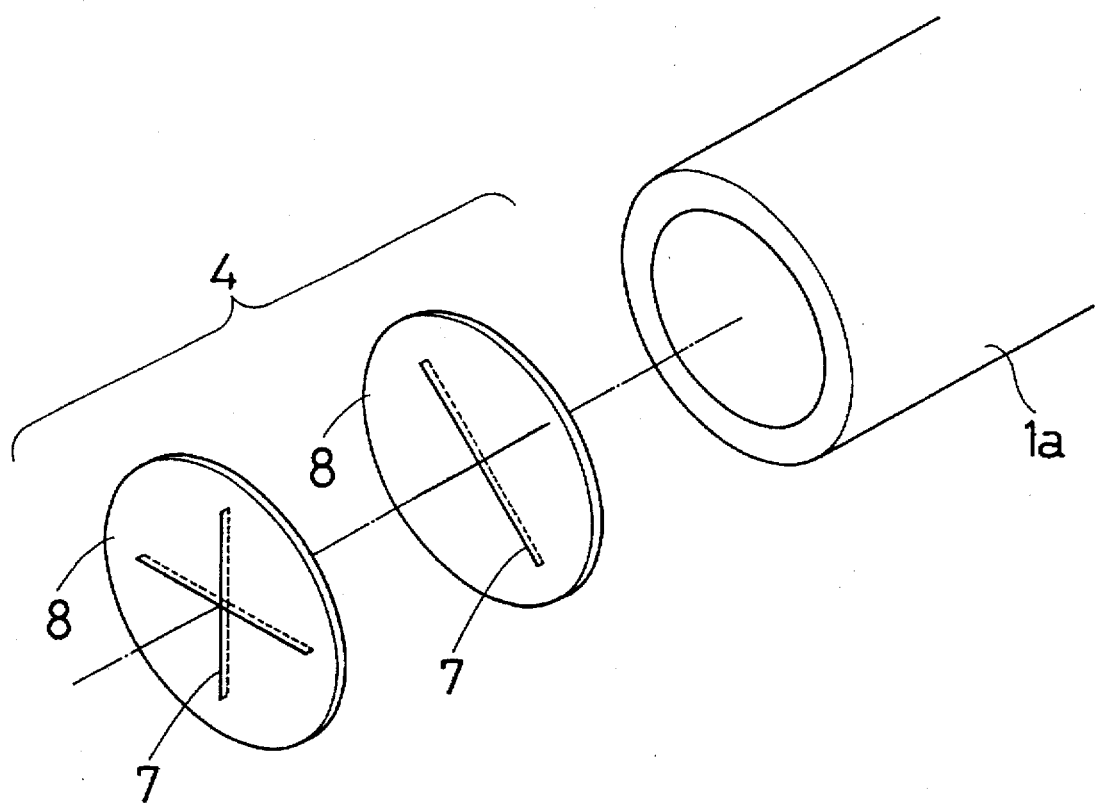
FIG. 7 is an explanatory view showing structure of a valve provided at the tip portion of the catheter in the second embodiment of the urine occult blood test apparatus of the present invention.

Referring to FIG. 7, the openable valve 4 is fabricated by laminating a plurality of flexible thin films 8. Respective films have straight, cross or other shaped cuts 7 (cross cut in this embodiment) in the middle and are laminated in a manner that cuts do not coincide with each other. The valve 4 has a mechanism to open and close as the tip portion of the wire 1b comes in and out of the tip portion of the catheter 1a. As far as the valve 4 has such a mechanism, structure is not limitative to the above.

Figure 8:
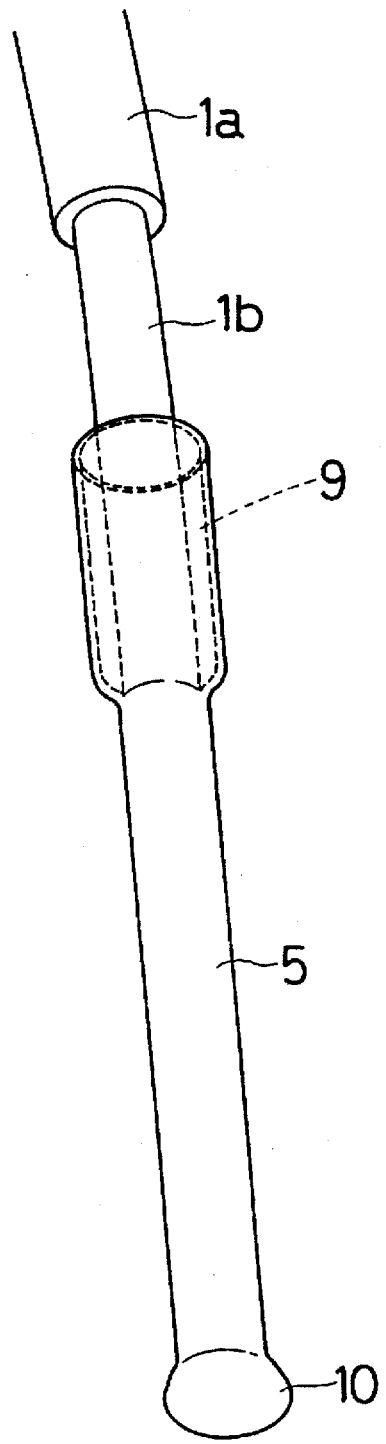
FIG. 8 is an explanatory view showing structure of an operation member at a rear end portion of the wire in the second embodiment of the urine occult blood test apparatus of the present invention.

The operation member 5 is affixed to the rear end portion of the wire 1b. As shown in FIG. 8, the operation member 5 includes a press-fit member 9 for the rear end portion of the catheter 1a and a bump 10 at the most rear end for easy catch and manipulation. The press-fit member 9 is to press and receive the rear end portion of the catheter 1a when using the urine occult blood test apparatus, and maintain a state in which the tip portion of the wire 1b is being projected and exposed from the tip portion of the catheter 1a.

The urine occult blood test apparatus of the present invention as stated above is used in the following manner.

First, a cystoscope is inserted transurethrally, and urine in a bladder is discharged. In one of the bifurcate working channels of the cystoscope, a ureteral catheter is inserted, and remaining urine is discharged. Subsequently, harmless gas such as air and carbon dioxide is charged through the ureteral catheter to fill the bladder.

Next, in case of the first embodiment of the urine occult blood test apparatus of the present invention, the catheter 1a is inserted in the other working channel of the cystoscope, and advanced to just before a ureteral opening. At this stage, the soluble substance 3 covering the urine occult blood test member 2 is dissolved and the urine occult blood test member 2 is exposed. In this state, urine coming out from either the right or left ureteral opening is received at the tip portion of the catheter 1a with direct observation. And with direct observation of the discoloration of the urine occult blood test member 2 held at the tip portion of the catheter 1a by cystoscope, a urine occult blood test is conducted.

Figure 9:
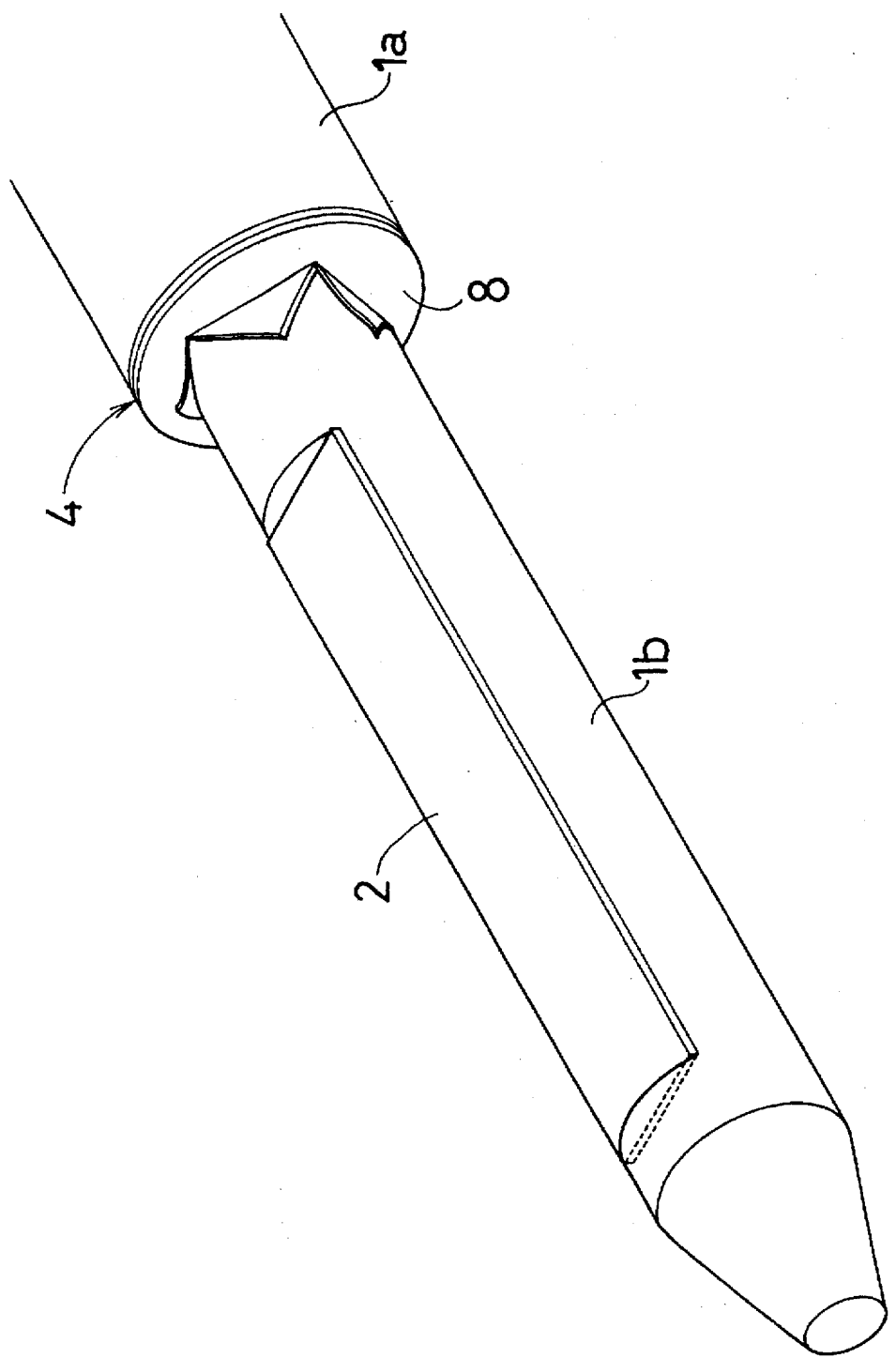
FIG. 9 is a magnified perspective view showing a state in which the tip portion of the wire is projected from the tip portion of the catheter in the second embodiment of the urine occult blood test apparatus.

In case of the second embodiment of the urine occult blood test apparatus of the present invention, with the tip portion of the wire 1b being buried in the tip portion of the catheter 1a, the catheter 1a is inserted in the other working channel of the cystoscope and advanced to just before the ureteral opening. Then, by manipulation of the operation member 5, the tip portion of the wire 1b comes out from the tip portion of the catheter 1a, as shown in FIGS. 3 and 9. Under direct observation, urine coming out from either the right or left ureteral opening is received in the tip portion of the wire 1b with the urine occult blood test member 2.

Figure 10:
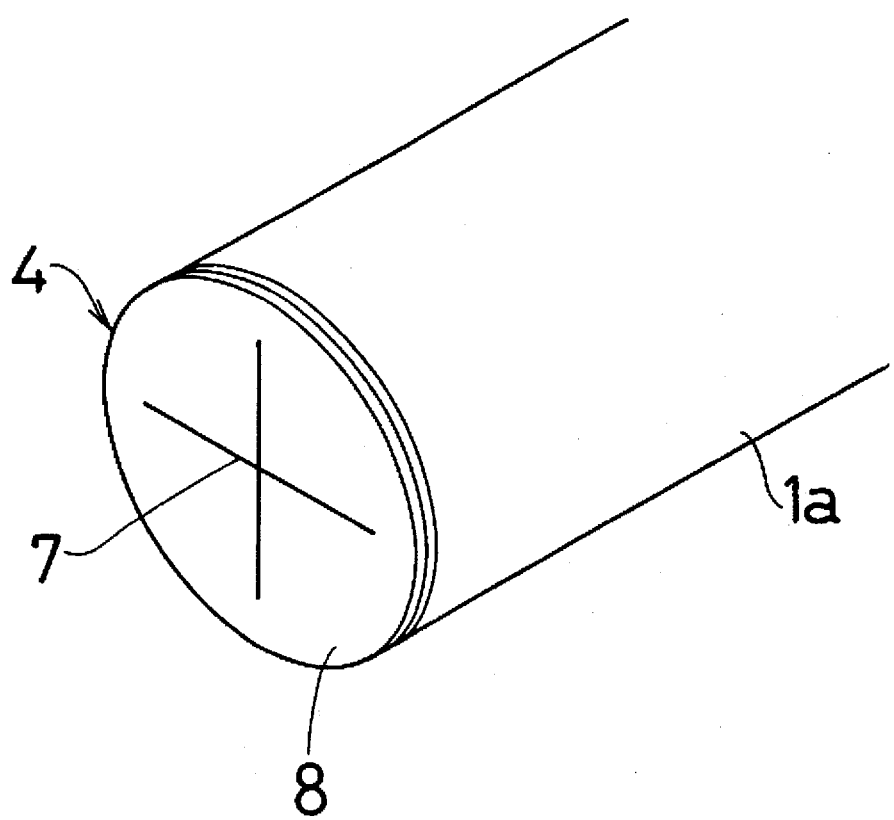
FIG. 10 is a magnified perspective view showing a state in which the tip portion of the wire is retracted in the tip portion of the catheter in the second embodiment of the urine occult blood test apparatus of the present invention.

Afterwards, by further manipulation of the operation member 5, the tip portion of the wire 1b is retracted in the tip portion of the catheter 1a, as shown in FIGS. 4 and 10, and then the urine occult blood test apparatus of the present invention is drawn out. By observing discoloration of the urine occult blood test member 2, urine occult blood is tested.

Alternatively, without the above further manipulation of the operation member 5, the tip portion of the wire 1b being kept exposed, the discoloration of the urine occult blood test member 2 may be directly observed by the cystoscope in the same way as in the first embodiment stated above.

The urine occult blood test apparatus of the present invention, which is constituted as stated above, is inserted to just before a ureteral opening by using a cystoscope. It is directly observed that urine coming out from the ureteral opening is received by the tip portion of the insert member 1 having the urine occult blood test member 2. Therefore, conducting such a urine occult blood test enables to confirm which is bleeding, the right or left kidney or the right or left ureter.

What is claimed is:

1. A urine occult blood test apparatus comprising:

an elongated catheter (1a) insertable in a working channel of a cystoscope;

a urine occult blood test member (2), said test member (2) being provided on a surface of a tip portion of said catheter (1a) and covered with a substance (3) harmless to a human body and soluble in several minutes after insertion into a human body; and wherein said test member (2) is covered with said substance (3) during insertion, but exposed after positioning near a ureteral meatus due to solution of said substance (3) and existence of urine occult blood near the ureteral meatus can be tested.

2. A urine occult blood test apparatus according to claim 1, wherein said substance (3) is a starch.

3. A urine occult blood test apparatus according to claim 1, wherein said test member (2) is received in a groove (6) provided on a surface of said catheter (1a).

4. A urine occult blood test apparatus according to claim 3, wherein said test member (2) is a urine test paper adhered to said groove (6).

5. A urine occult blood test apparatus comprising:

a catheter (1a) insertable in a working channel of a cystoscope and having a valve (4) in a tip portion;

a wire (1b) slidably inserted in the catheter (1a) and projectable out from and retractable into said tip portion of said catheter (1a) through said valve (4);

a urine occult blood test member (2) covered with a substance (3) harmless to a human body and soluble in several minutes after insertion into a human body provided at a tip portion of said wire (1b);

an operation member for said wire (1b); and wherein operating said operation member allows said test member (2) to be kept in said catheter (1a) during insertion, and to move out from said catheter (1a) after positioning near a ureteral meatus and existence of urine occult blood near the ureteral meatus can be tested.

6. A urine occult blood test apparatus according to claim 5, wherein the test member (2) is a urine test paper received in a groove (6) on a surface of said tip portion of said wire (1b).

7. A urine occult blood test apparatus according to claim 5, wherein said valve (4) is made up of plural flexible thin films (8) having cuts in respective center portions and layered such that the cuts do not match with each other.

* * * * *